United States Patent

Jansen

Patent Number: 6,113,631
Date of Patent: Sep. 5, 2000

[54] MITRAL VALVE PROSTHESIS

[75] Inventor: Josef Jansen, Köln, Germany

[73] Assignee: Adiam Medizintechnik GmbH & Co. KG, Erkelenz, Germany

[21] Appl. No.: 09/180,604

[22] PCT Filed: Jun. 18, 1997

[86] PCT No.: PCT/DE97/01298

§ 371 Date: Nov. 10, 1998

§ 102(e) Date: Nov. 10, 1998

[87] PCT Pub. No.: WO97/49356

PCT Pub. Date: Dec. 31, 1997

[30] Foreign Application Priority Data

Jun. 24, 1996 [DE] Germany .............................. 196 24 948

[51] Int. Cl.[7] .................................................. A61F 2/06
[52] U.S. Cl. ........................................ 623/2.17; 623/2.19
[58] Field of Search ............................. 623/2, 900, 2.15, 623/2.16, 2.17, 2.18, 2.19, 2.38, 2.41

[56] References Cited

U.S. PATENT DOCUMENTS

| | | | |
|---|---|---|---|
| 4,084,268 | 4/1978 | Ionescu et al. | 623/2.15 |
| 4,222,126 | 9/1980 | Boretos et al. | 623/2.19 |
| 5,376,113 | 12/1994 | Jansen et al. | 623/2 |
| 5,449,385 | 9/1995 | Religa et al. | 623/2 |
| 5,500,016 | 3/1996 | Fisher | 623/2.19 |
| 5,800,527 | 9/1998 | Jansen et al. | 623/2 |
| 5,824,062 | 10/1998 | Patke et al. | 623/2 |
| 5,855,602 | 1/1999 | Angell | 623/900 X |

FOREIGN PATENT DOCUMENTS

| | | |
|---|---|---|
| 0 363 753 | 4/1990 | European Pat. Off. . |
| 23 55 959 | 6/1975 | Germany . |
| 38 34 545 C2 | 4/1990 | Germany . |
| 42 22 610 A1 | 1/1994 | Germany . |
| WO 93/18721 | 9/1993 | WIPO . |

*Primary Examiner*—Michael J. Milano
*Assistant Examiner*—Brian E. Pellegrino
*Attorney, Agent, or Firm*—Herbert Dubno

[57] ABSTRACT

A mitral valve prosthesis consists of a support housing (stent) with a base ring that bears at least two stays which substantially extend in the ring axis direction and are connected by curved wall for securing two flexible cusps. In order to obtain as uniform and reduced forces as possible between the cusps and the support housing, the connection lines between the cusps (21 to 23) and the top inner edge (241) of the wall (24) lie each in a plane.

10 Claims, 6 Drawing Sheets

MITRAL VALVE PROSTHESIS

CROSS REFERENCE TO RELATED APPLICATIONS

This application is a national stage of PCT/DE 97/01298 filed Jun 18, 1987 and based upon German National Application 196 24 948.1 filed Jun. 24, 1996 under the International Convention.

FIELD OF THE INVENTION

The invention relates to a prosthetic heart valve comprised of a support housing (stent) with a base ring which has at least two posts extending substantially in the axial direction of the ring and connected by an arcuate wall serving to fasten two flexible cusp-shaped leaflets.

BACKGROUND OF THE INVENTION

Such a construction is known for example from DE 38 34 545 C2. The support housing disclosed there is comprised of a cylindrical base ring which is extended by three posts tapering in the axial direction and offset respectively about the periphery by 120°. The end wall surfaces which lie between the posts serve to receive and secure three cusps [leaflets] which ensure the closing and opening of the heart valve. In the closed state, the cusp-shaped leaflets lie against each other at their free edges with the formation of an overlapping region. This construction as well as that of the construction described in DE 42 22 610 closely resembles the natural aortic valve in which the connection line between the cusp-shaped leaflet with the natural aorta root approximates the intersection of a cylinder with the aortic vessel. In this region the connection line closes the downstream side commissures in which the lines or the cusp-shaped leaflets lie. These commissures prevent the inversion of the cusp-shaped leaflets and serve in combination with the cusp-shape leaflet overlapping regions for bracing the opposing cusp-shaped leaflets.

To reduce the high stresses in the commissure regions, i.e. in the region of the posts, these must be formed so as to be flexible especially in their upper parts. There is however the danger that because of closing pressure differences excessive deformation will arise which can finally lead to creeping and as a consequence, to premature fatigue.

OBJECT OF THE INVENTION

It is the object of the present invention to provide a prosthetic heart valve of the originally described type in which the forces arising between the cusps-shaped leaflets and the support housing are uniformly limited to the smallest possible.

SUMMARY OF THE INVENTION

These objects are attained with the prosthetic heart valve which is characterized in that the connection line of the cusp leaflet with the upper inner edge of the wall lies in a plane. The region between the posts along which the connection line runs is therefore not, as is known from the state of the art, any longer bulged three dimensionally, but rather lies in a plane whereby the connection curve is formed by the intersection of a plane inclined relative to the longitudinal axis of a cylinder with this cylinder. Because of this feature, upon opening and closing of the three cusp-shaped [leaflets], high stresses can be effectively avoided, especially in the regions of the post tips. Simultaneously it can be ensured that the transition of the cusp-shaped leaflet between its open and closed position is improved, thereby significantly increasing the functional reliability of the heart valve. The overlapping surfaces of the heart valve with three cusp-shaped leaflets can be significantly reduced by the cusp-shaped leaflet connection according to the invention so that folding of the cusp-shaped leaflet surfaces lying against one another in the closed state can be avoided.

The configuration according to the invention is useable also with two cusp-shaped leaflet heart valves as well as with the three cusp-shaped leaflet heart valve.

The walls between the posts can be configured as solid surfaces or as strips or as is described for example in DE 42 22 610 A1. The end surfaces of the wall for the cusp-shaped leaflet attachment can be beveled outwardly in the radial direction, thereby simplifying the fastening of the cusp-shaped leaflets to the respective surfaces.

Especially with heart valves having two cusp-shaped leaflets, although also with three cusp-shaped leaflet heart valves, the posts form at their free ends, a prismatic inner support for the cusp-shaped leaflets. The post end surfaces are then substantially triangular shaped so that the cusp-shaped leaflets with their free edges can lie against one another without fold formation to seal well in the closed state.

Preferably the thickness of the wall, i.e. the wall thickness in the region of the cup base, i.e. between the posts, is greater at posts or in the post regions. In this manner, the support housing is stiffened radially and axially in the sense of uniform loading without diameter constriction, thereby enabling an advantageous ratio of the flow cross section to the total cross section to be achieved. The post ends can be thickened both with two cusp-shaped leaflet heart valves and with three cusp [leaflet] heart valves by material accumulation, as has been described basically in DE 42 22 610 A1 in conjunction with a three cusp-shaped leaflet valve.

A further advantageous combination according to the invention of the connection line of the cusp-shaped leaflet with the inner edge of the wall, with the connection line lying in a plane for a two cusp-shaped leaflet mitral heart valve, can be realized as follows:

The mitral heart valve having a support housing with a base ring can be characterized in that the base ring, seen in plan view, is comprised of a shape assembled from two semiellipses with a common longitudinal axis, but two half transverse axes of unequal length, whereby the posts lie on the longitudinal axis and form the transition location from one to the other semiellipse, and whereby the wall has a semielliptical curvature which is inclined to the base ring base surface more strongly and carrying a reduced area cusp-shaped leaflet, than the wall with greater curvature. The two semiellipses thus form a stent body which largely approximates the natural mitral valve of a heart which has a D shape or kidney shape. To the extent that, for example, in U.S. Pat. No. 5,415,697 so-called biological mitral valves without stents are described, these have the difference by comparison with the mitral heart valve of the invention, that the aortic cusp-shaped is on the side with reduced curvature while the mural cusp-shaped leaflet lies in the regions having a greater curvature.

Preferably the cusp-shaped inclination which is determined by the orientation of the connection line of the cusp-shaped leaflet with the upper inner edge of the wall, always lies at 40° and 55° for the lesser inclined (aortic) cusp [leaflet] and between 25° and 45° for the more strongly inclined (mural) cusp-shaped each relative to the base surface. The more strongly inclined cusp-shaped leaflet has at least 5° greater angular setting then the lesser inclined cusp-shaped .

According to a further feature of the invention, the main flow direction is inclined by about 10° to 20° preferably about 15°, from the normal to the mural cusp-shaped. This feature reduces the risk of interference and a possible injury to the support housing and to the surrounding heart chamber in the wall. The cusp-shaped leaflets form a funnel-shaped opening passage with a reduced cross section by comparison to an aortic valve. The described arrangement and configuration ensure a physiologically satisfactory flow from the atrium into the ventricle. The illustrated heart valve according to the invention can be fabricated in a smaller height than is possible with an embodiment known from the state of the art. This applies especially with reference to the circular cross section or the semielliptical shaped cross section of the housing.

In a preferred embodiment, the lengths of the half transverse axes of the semiellipses of the support housing are in a ratio of 1:5 to 2.5:1. Especially with a half axis ratio of 2:1, is it possible to bring about a shape largely equivalent to that of the naturally mitral valve.

The common longitudinal axis of the two different semiellipses of the support housing has a length between 10 mm and 45 mm.

Preferably the posts are integrated into the wall with the same thickness as the wall, i.e. the described posts or stays do not project out of the wall regions and the wall rather runs in the region of each post upwardly preferably to a tip for flattened post ends. As has been described in principle already in DE 42 22 610 A1, the posts, as an alternative to the aforedescribed embodiment, can be configured prismatically. According to the invention they have at their upper free ends respective substantially triangular end surfaces, whereby the triangle vertices are oriented toward one another. Preferably the end faces have substantially the form of equilateral triangles, whereby the triangle bases terminate in the outer (rounded) wall of the support housing. The bases in cross section, according to a further embodiment of the invention, are configured in triangle shapes over their entire lengths and thicken toward the free ends to the aforementioned end surface dimensions, preferably continuously. Inversely, the posts taper wedge-shaped toward the base ground surface whereby in the inlet region, i.e. ahead of the lower edge of the base ring, the end in transition into the base ring wall thickens there. The end surfaces project with their tips by about the measure of the triangle altitude into the flow cross section so that it is about 8% to 32% of the length of the common longitudinal axis of the support body. The end surface-triangle bases which merge with the wall have for example, a width between 2 mm and 8 mm.

To prevent deformation of the support housing upon opening and closing of the cusp-shaped leaflets corresponding to the pressure difference which is developed, the thickness or wall thickness of the wall of the base ring in the regions between the posts, i.e. at the bases of the cusp-shaped leaflets is greater than in the region near the posts; preferably the thickness is chosen to be greater by a factor of 1.4 to 2.3.

To prevent excessive strain on the valve cusp-shaped leaflets in the commissure region, according to a further feature of the invention, the connection lines of the cusp-shaped leaflets with the upper inner edges of the wall on each side are so oriented that they lie in a plane with this configuration of the end surface of the wall which serves for affixing the cusp-shaped leaflet, high stresses are avoided.

If the posts of the support body are so arranged that their longitudinal axes are inclined somewhat in the direction of the main flow direction, i.e. about 10° to 25° with respect to the base surface, the mitral valve can be further improved with respect to the flow cross section, the structural height and its stability.

The described mitral heart valves can avoid numerous structurally-based and material-based risks characterizing known embodiments from the state of the art. With the construction according to the invention, the mitral heart valves achieve a close approximation to the shape of the natural mitral valve. By comparison to bioprostheses as mitral valve replacements which require the treatment of the patients with anticoagulant medicaments in 50% of the cases, the mitral valve prosthesis of the invention can function medicament-free since the flow path formed by the combination and cusp-shaped leaflet settings and the open cross section minimize the effect on flow direction and mechanical damage to the blood.

BRIEF DESCRIPTION OF THE DRAWING

The above and other objects, features, and advantages will become more readily apparent from the following description, reference being made to the accompanying drawing in which.

SPECIFIC DESCRIPTION

The heart valve shown in FIGS. 1–6 are comprised in general of a support housing 20 as well as three cusp-shaped leaflets 21–23 which are fastened to radially outwardly oriented inclined surfaces 24 of the end face of the wall 25. The support housing 20 is comprised substantially of a base ring 26, whose diameter determines the throughput of the valve. The wall 25 is oriented substantially perpendicular to the base ground surface, whereby three peaks as posts or stays project with angular spacings of 120° from one another and between which the end face 24 of the wall runs in circular arc shapes. The inner edge 241 of these end faces lie respectively in planes which are defined as intersection lines of a cylinder with a plane inclined to its longitudinal axis. The result is a setting angle of three planes of about 80° to the base ring ground surface. The support housing is comprised of an elastic synthetic resin. It can be a thermoplast like a polyamide which is produced for example by injection molding and after roughening of the outer surface is coated with polyurethane. The cusp-shaped leaflets 21–23 are comprised of a flexible thin synthetic resin foil which preferably also is made from polyurethane.

Figure 1:
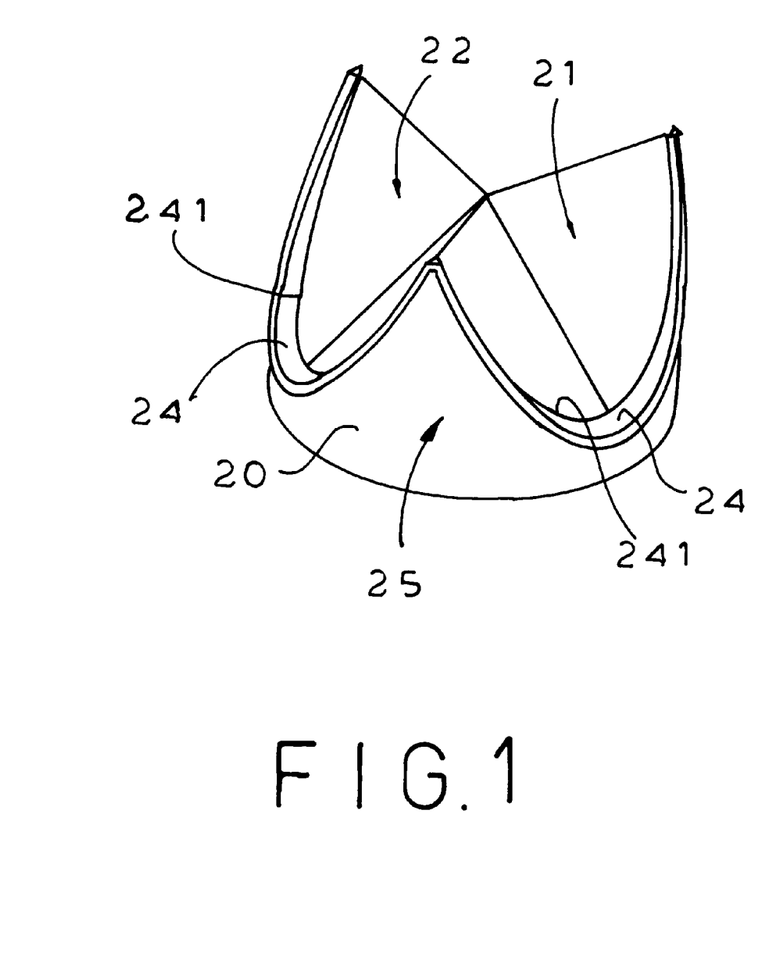
FIGS. 1 and 2 are respective perspective views of a three-cusp-shaped leaflet heart valve.
Figure 2:
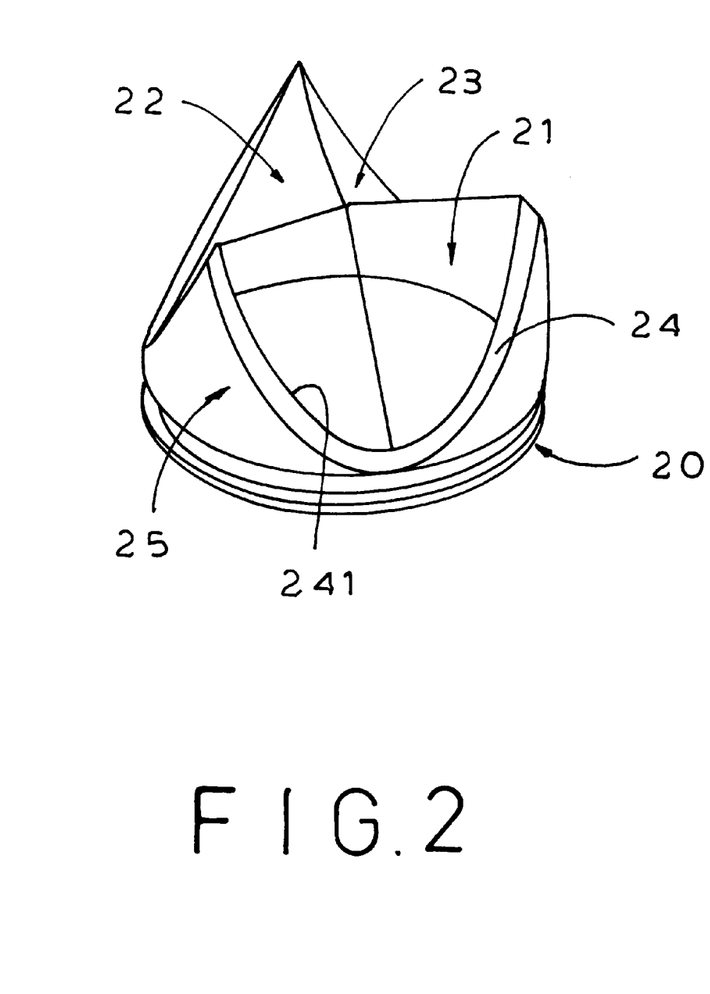
Figure 3:
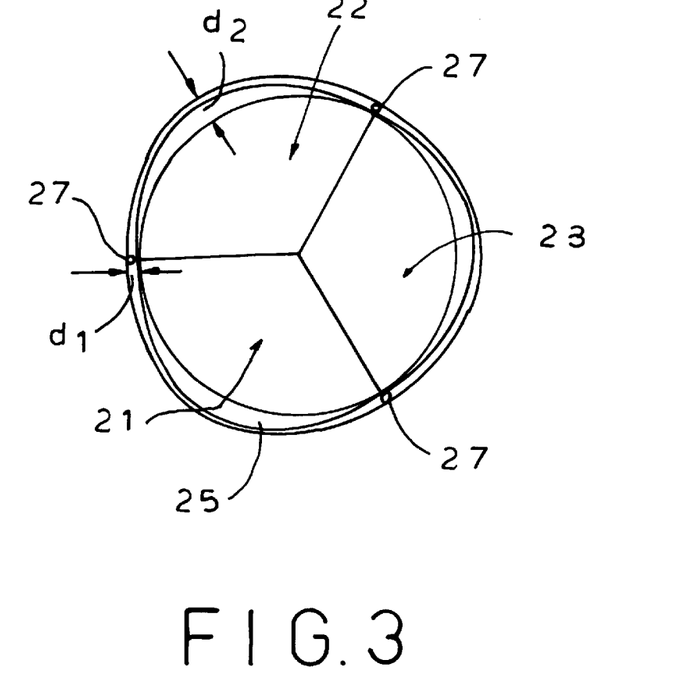
FIG. 3 is a plan view of the heart valve of FIGS. 1 and 2.
Figure 4:
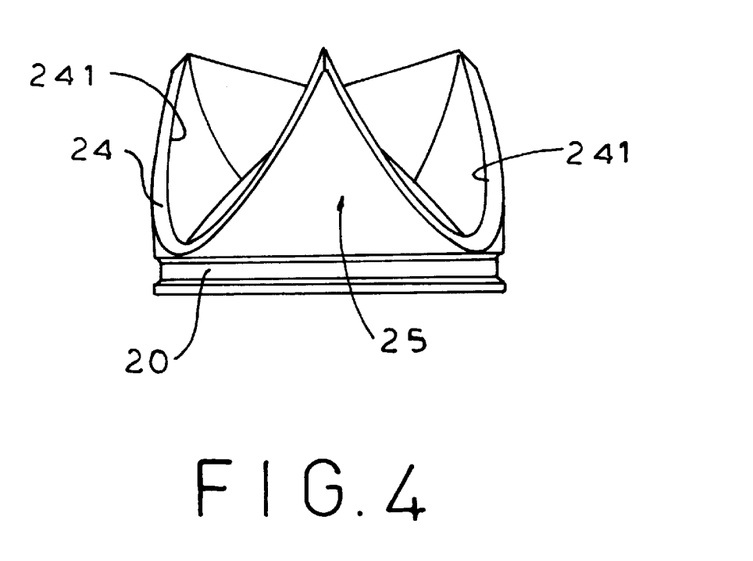
FIGS. 4 and 5 are respective side elevational views of this heart valve.
Figure 5:
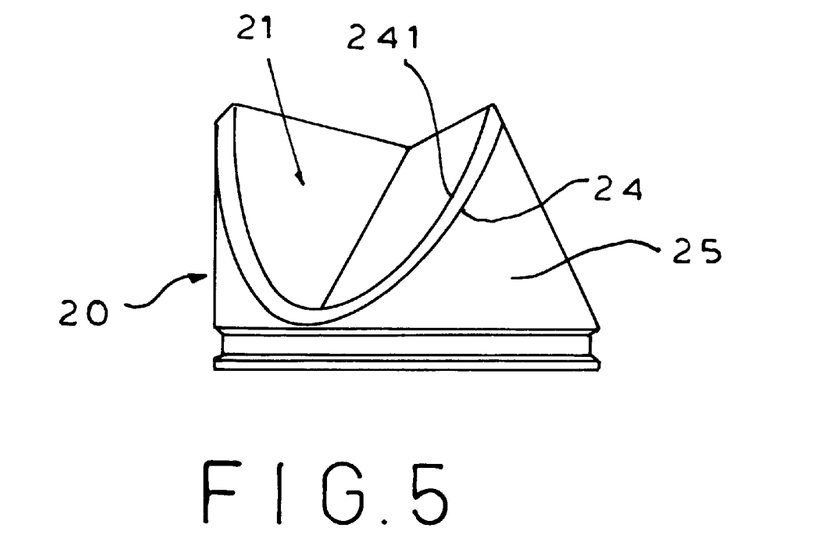
Figure 6:
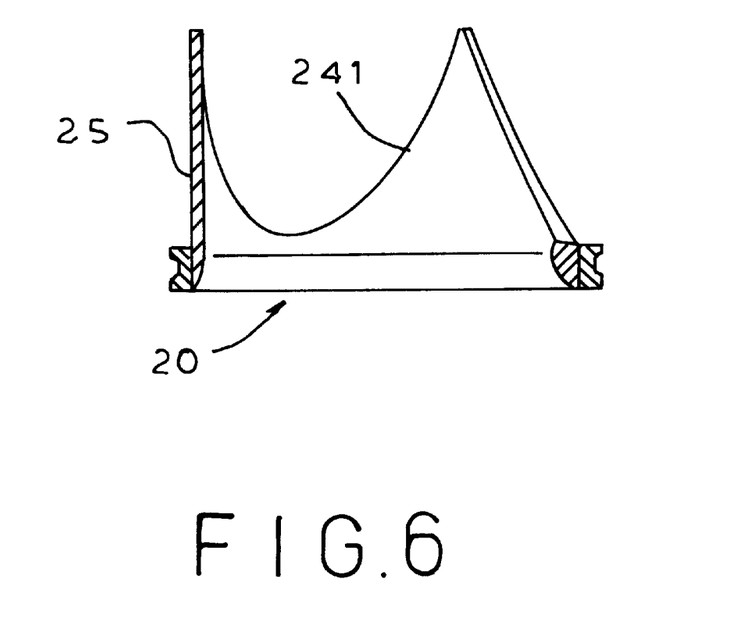
FIG. 6 is a cross sectional view of the heart valve shown in FIGS. 1–5 along the line VI—VI in FIG. 3.
Figure 7:
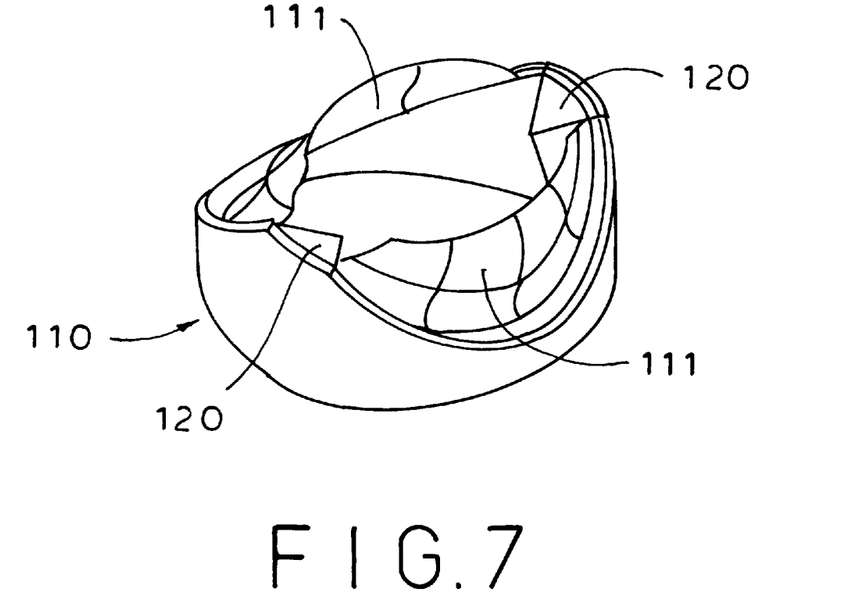
FIG. 7 is a perspective view of a two-cusp-shaped leaflet heart valve (mitral heart valve)
Figure 8:
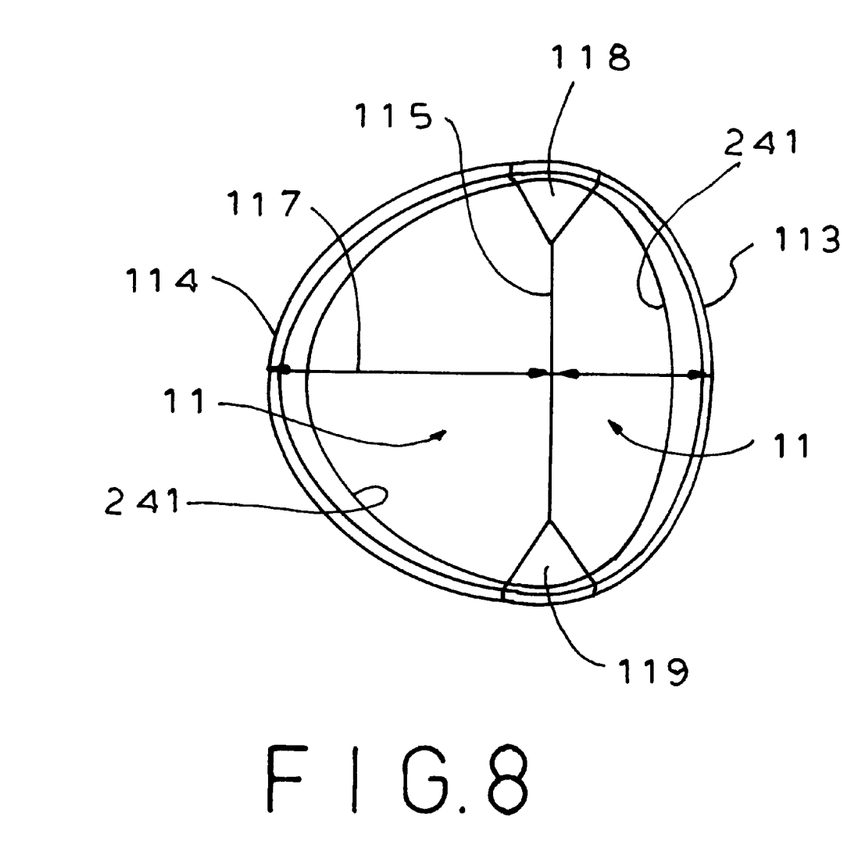
FIG. 8 is a plan view of this heart valve according to FIG. 7.
Figure 9:
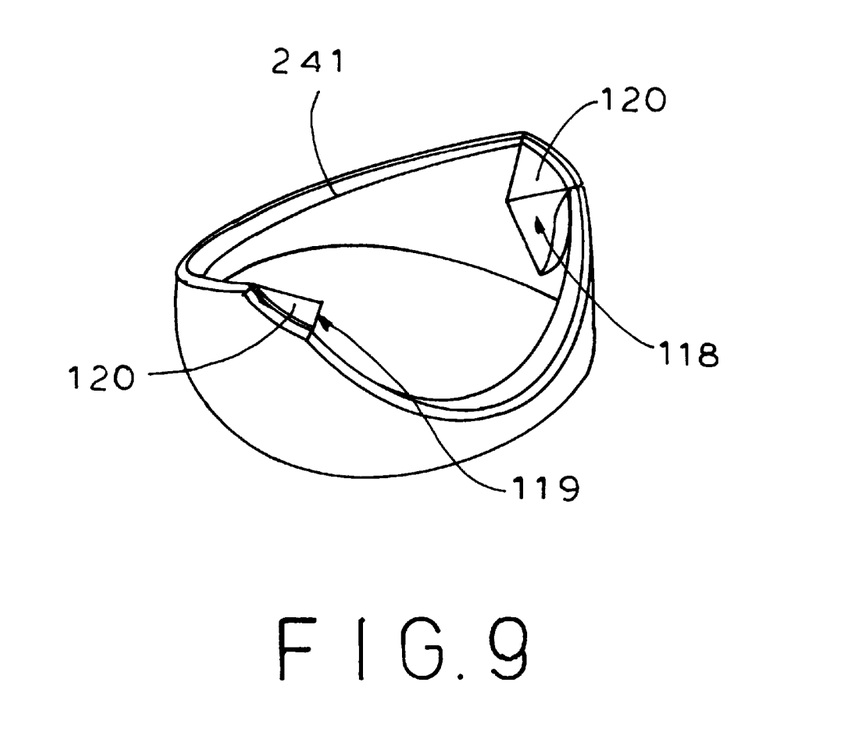
FIG. 9 a perspective side view of the support housing (without cusp-shaped.
Figure 10:
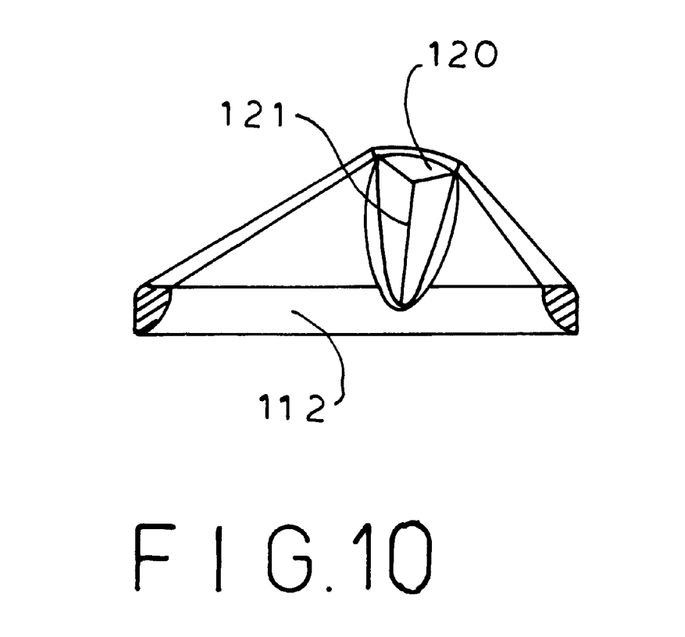
FIG. 10 is a section along the line X—X of FIG. 8 (without cusp-shaped leaflets, FIG. 11 is a perspective view of a further mitral heart valve.

As can especially be seen from FIG. 3, the thickness of the wall 25 between the posts 27 is greater than in the region of the posts. The posts 27 themselves can form on their end faces prismatic inner seats for the cusp-shaped leaflets 21–23. The post end faces can be triangular, optionally in the manner described in DE 42 22 610 A1.

The mitral heart valve illustrated in FIGS. 7–10 represents an alternative two-cusp shaped leaflets embodiment. The prosthetic mitral heart valve is comprised of a support housing 110 which has two cusp-shaped leaflets 111. The support housing 110 is sutured by means of a suture ring in the annulus of the patent tissue. The support housing 110 is comprised of a thermoplast like polyurethane which is formed into a slightly bendable elastic body, for example by injection molding. The one-piece support housing 110 has a base ring 111 whose inner edges are rounded from the exterior inwardly in a manner known from the state of the art. For better attachment of the suture ring (not shown), the base ring can have on its outer surface a bulge. The wall which is substantially perpendicular to the base ring base surface is subdivided into a first wall portion 113 of reduced curvature and a second wall portion 114 of greater curvature and which together, in a plan view, upon the base ground surface, define two semiellipses with a common longitudinal axis 115. Since the two half transverse axes 116 and 117 are of different lengths, preferably their length ratio can amount to 1:2. The outer wall of the wall portions 113 and 114 is smooth, curved and flush up to a bulge in the region of the base ring. The same applies with the exclusion of the posts 118, 119 to be described below, for the inner surface of the wall portions 113 and 114.

The wall thicknesses of the wall portions 113 and 114 differ and reduce toward the regions approaching the posts and is greatest in their intermediate regions. Preferably the wall thickness in each intermediate region between the posts is twice that of the thickness in the region proximal to the post. The upper end face of the wall portions 113 and 114, to which the cusp-shaped leaflets are fastened, are inclined outwardly and run substantially to the region of the posts in the form of an intersection line which is defined by the intersection of the respective upper inner edge of the wall portion 113 and 114 lines in a plane which runs at an angle of about 50° to the base ring ground surface for the upper edge of the wall portion 113 or at an angle of 35° with the base ring ground surface for the upper edge of the wall portion 114. The arrangement of the upper inner edges of the wall portions 113 and 114 in planes at different angles, gives the advantage that both cusp-shaped leaflets can be cut from a flat sheet of synthetic resin foil and can be cemented without tension stresses and without the danger of fold formation on the upper edges of the walls up to the regions adjoining the posts.

The material for the cusp-shaped leaflets can be a synthetic resin foil in accordance with the state of the art, preferably a foil of flexible polyurethane.

The posts 118 and 119 have a prismatic contour and widen uniformly to their upper end faces 120 which is configured substantially in triangular shape. In a plan view on the inner wall of the support housing 110, the posts appear to be configured in V shape and end wedge-like above the base ring ground surfaces in an inlet region of the support housing 110. The cross sections of the posts 118, 119 parallel to the base ring ground surface form substantially equilateral similar triangles whereby the post longitudinal axes 121 with respect to the base ring ground surface are not vertical but slightly inclined to a surface normal, preferably under an angle of 15°. A corresponding inclination of preferably 15° applied also to the end face 120 of the posts with respect to the base ring ground surface.

The end faces 120 of the posts form a triangle with a base curved correspondingly to the transition contour between the walls 113 and 114 and to approximately equilength outer shanks so that the tips of the end faces of the two posts 118 and 119 are turned toward one another. The posts 118, 119 or their end faces 120 replace the commissure regions of the natural valve and serve with their approximately equilateral triangular shanks as prismatic inner seats for the cusp-shaped leaflets 111. In the transition region between the equilength triangular shanks and the walls 113 and 114, the support housing is rounded. The cusp-shaped leaflets 111 are adhesively bonded to the upper edge walls 113 and 114 up until this rounded region with the support housing are so cut that, in the closed state they rest against the lateral equishank post edges and in the regions lying between the posts lie approximately linearly against the opposing cusp-shaped leaflets. The commissure regions formed by the posts 118 and 119 prevent a breakthrough of the cusp-shaped leaflets and serve together with the overlapping region of the cusp-shaped leaflets 111 running along the longitudinal axis as a cusp-shaped leaflets bracing. Because of the connection line of the cusp-shaped leaflets 111 to the wall 113 and 114 lying in a plane up to the commissure regions, a uniform force distribution is provided between the cusp-shaped leaflets 111 and the support housing 110 so that especially high radial tensile stresses are avoided at the post ends or in regions close to the post which can give rise, in conventionally known constructions to material gathering of the support housing and so-called creeping.

The configuration of the support housing 110 is matched to the natural D shape or kidney shape as far as possible, whereby the mural cusp-shaped leaflets is arranged on the upper edge of the wall 113 at a relatively more steep setting angle and the mural cusp-shaped leaflets is arranged on the wall 114 with a flatter setting. As a result a reduced structural height of the mitral heart valve is possible whose main flow direction is not coaxial but rather is inclined by about 15°.

Figure 11:
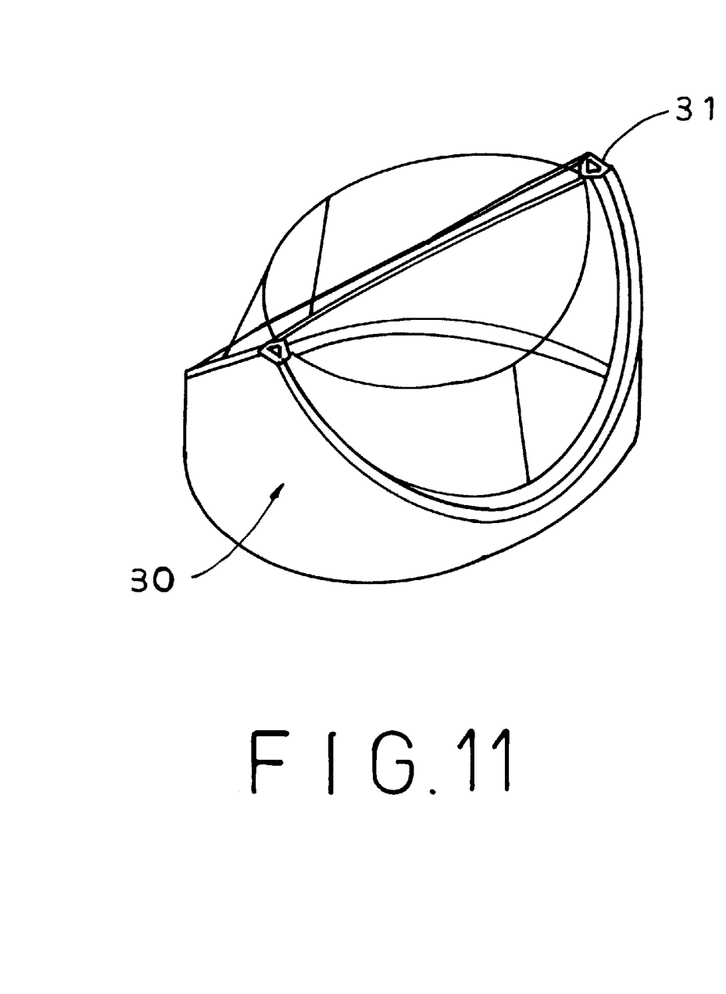
Figure 12:
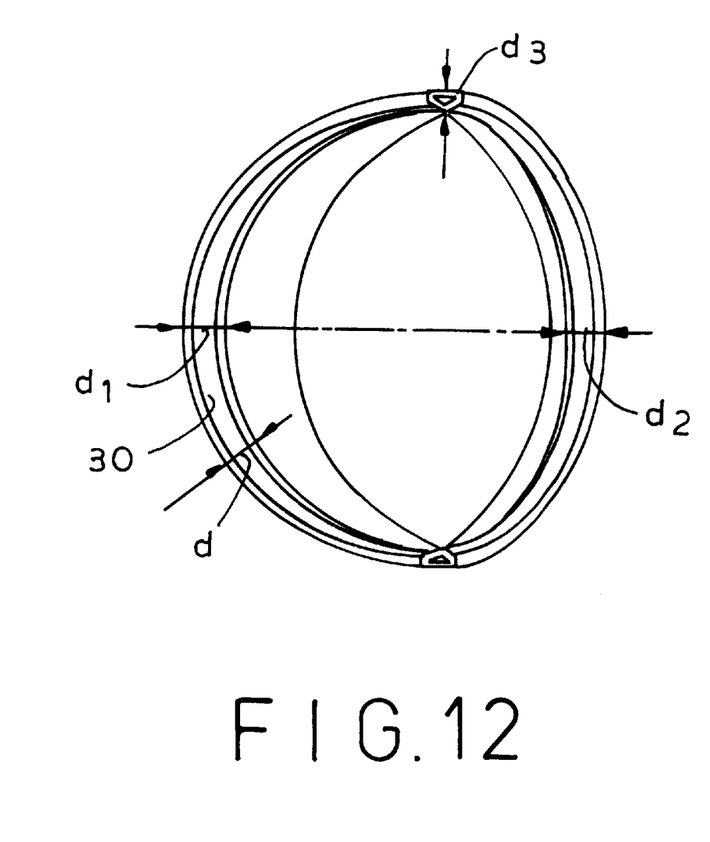
FIG. 12 a plan view of this heart valve according to FIG. 11.

FIG. 11 shows an alternative embodiment of a mitral heart valve in which the aforedescribed posts are no longer manifested bodily. Rather in this embodiment the posts are integrated into the wall 30 and are of equal thickness therewith. The wall runs on opposite ends upwardly to an end-side post end 31 which can be bonded or as shown, flattened. The thickness of the wall d can continuously diminish from the base ring to the upper edge of the wall. As is more readily apparent from FIG. 12, the thickness d of the wall 30, measured at the level of the base ring is a minimum in the region of the posts and grows to a maximum value. In a concrete embodiment, the thickness $d_1$ is 2.57 mm, the thickness $d_2$ is 2.34 mm and the thickness $d_3$ (in the region of both posts) is 1.4 mm.

In the production of the heart valve described, each fabricated cusp-shaped leaflets is affixed by itself bonding or welding on the end face of the support housing. Alternatively, it is also possible to produce the heart valve by means of an injection molding technique known in the art, including two component injections, in which initially the support housing is made and then the cusp-shaped leaflets are applied by injection molding. A further possibility is the use of the so-called immersion technique. In this case, a support housing for example a polyamide is provided with a coat of polyurethane on a corresponding immersion mandrel with forming surfaces for the cusp-shaped leaflets and on to which the support housing has been shoved. Then an immersion mandrel with the support housing is immersed in a liquid synthetic resin solution (polyurethane) and tumbled therein for a sufficient length of time until the desired thickness distribution is achieved. During the tumbling the synthetic resin hardens.

The invention applies also to artificial blood pumps (artificial hearts), conduit valve implants, bioprostheses or mechanical prostheses and the like, in which the support housing is an integrated component of a tubular housing or hose.

What is claim is:

1. A prosthetic heart valve comprising:

a base ring adapted to be secured in heart tissue and surrounding a flow cross section, said base ring lying in a base plane;

a valve housing connected to said base ring and formed with at least two posts spaced-apart around said ring and extending substantially in an axial direction with respect to said ring, and a wall extending axially from said base ring between said posts and rising arcuately from said base ring to apexes at said posts, said wall having end faces between the posts inclined radially outwardly and toward said base plane, said end faces having inner edges; and respective cusp-shaped leaflets attached to said wall along each of said inner edges in an arcuate connecting line lying in a respective connecting line plane and corresponding to an intersection between the respective connecting line plane and a cylinder to an axis of which the connecting line plane is inclined, said leaflets meeting within said housing for closure of said valve.

2. The prosthetic heart valve defined in claim 1 wherein said wall has a solid surface.

3. The prosthetic heart valve defined in claim 1 wherein said wall is formed from strips.

4. The prosthetic heart valve defined in claim 1 wherein said posts have prismatic configurations at least at free ends engaging said leaflets.

5. The prosthetic heart valve defined in claim 4 wherein said prismatic configurations are triangular with triangle vertices oriented radially inwardly.

6. The prosthetic heart valve defined in claim 1 wherein said wall has a thickness which is greater between said posts than at said posts.

7. The prosthetic heart valve defined in claim 1 wherein the thickness of said wall intermediate said posts has a ratio to the thickness in the region of said posts which is between 1.7:1 and 2.8:1 for a three leaflet valve and between 1.4:1 and 2.3:1 for a two leaflet valve.

8. The prosthetic heart valve defined in claim 1 wherein said valve has the configuration of a mitral valve with two posts and two leaflets.

9. The prosthetic heart valve defined in claim 1 wherein said valve is a three-leaflet valve having three posts angularly spaced apart along said ring and respective cusp-shaped leaflets between each pair of posts.

10. The prosthetic heart valve defined in claim 1, further comprising a suture ring affixed to said base ring for suturing said valve in said tissue.

* * * * *